United States Patent
Russell et al.

(10) Patent No.: US 9,744,114 B2
(45) Date of Patent: Aug. 29, 2017

(54) MODIFIED STARCHES FOR USE IN PERSONAL CARE APPLICATIONS

(75) Inventors: Michael Russell, Madison, NJ (US); Gary Theodore Martino, Monmouth Junction, NJ (US); Kendrick H. Horn, Doylestown, PA (US); Shawn R. Branning, Nazareth, PA (US)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 173 days.

(21) Appl. No.: 13/982,922

(22) PCT Filed: Feb. 2, 2012

(86) PCT No.: PCT/EP2012/051726
§ 371 (c)(1),
(2), (4) Date: Oct. 8, 2013

(87) PCT Pub. No.: WO2012/104362
PCT Pub. Date: Aug. 9, 2012

(65) Prior Publication Data
US 2014/0030196 A1 Jan. 30, 2014

Related U.S. Application Data

(60) Provisional application No. 61/439,116, filed on Feb. 3, 2011.

(30) Foreign Application Priority Data

Jun. 21, 2011 (EP) .................................. 11170650

(51) Int. Cl.
*A61Q 17/04* (2006.01)
*A61Q 1/12* (2006.01)
*A61Q 5/02* (2006.01)
*A61K 8/73* (2006.01)
*A61Q 19/00* (2006.01)
*A61K 8/02* (2006.01)
*A61Q 5/12* (2006.01)

(52) U.S. Cl.
CPC ............. *A61K 8/732* (2013.01); *A61K 8/022* (2013.01); *A61Q 19/00* (2013.01); *A61Q 1/12* (2013.01); *A61Q 5/02* (2013.01); *A61Q 5/12* (2013.01); *A61Q 17/04* (2013.01)

(58) Field of Classification Search
None
See application file for complete search history.

(56) References Cited

U.S. PATENT DOCUMENTS

| | | | | |
|---|---|---|---|---|
| 2,961,339 A * | 11/1960 | Wolff | | 427/212 |
| 3,071,492 A | 1/1963 | Satterly | | |
| 3,852,475 A * | 12/1974 | Tarangul | | 514/778 |
| 4,877,604 A * | 10/1989 | Schlossman | | A61K 8/25 424/63 |
| 5,071,978 A * | 12/1991 | Sau | | C08B 11/193 536/102 |
| 5,618,874 A * | 4/1997 | Jourbert | | C11D 3/1286 510/507 |
| 5,776,476 A * | 7/1998 | Billmers et al. | | 424/401 |
| 6,391,322 B1 * | 5/2002 | Roulier et al. | | 424/401 |
| 7,374,587 B2 | 5/2008 | Lewis | | |
| 7,375,214 B2 | 5/2008 | Lewis | | |
| 2007/0246179 A1 | 10/2007 | Silenius et al. | | |

FOREIGN PATENT DOCUMENTS

| | | | | |
|---|---|---|---|---|
| CA | 726667 A * | 1/1966 | | |
| CA | 726667 A | 1/1966 | | |
| EP | 0689829 A2 | 1/1996 | | |
| FR | WO 03049711 A2 * | 6/2003 | | A61K 8/046 |
| JP | 63-215616 A | 9/1988 | | |
| JP | 6-136002 A | 5/1994 | | |
| WO | WO 03049711 A2 * | 6/2003 | | |
| WO | WO 03/066016 A1 | 8/2003 | | |
| WO | WO 2005099651 A1 * | 10/2005 | | A61K 8/11 |

OTHER PUBLICATIONS

Susan K. Harlander. Safety Assessments and Public Concern for Genetically Modified Food Products: The American View. Toxicologic Pathology, vol. 30, No. 1, pp. 132-134, 2002.*
M. Canavari and P. Lombardi. European Consumer Attitudes Towards Thai Organic Rice and Tapioca: Focus Groups Results. Copyright 2007. pp. 3-9.*
Abstract of JP 6-136002.
Abstract of JP 63-215616.
O.B. Wurzburg, M.S., Modified Starches: Properties and Uses, CRC Press, 1986, Chapters 2-9.
Search Report of corresponding European Patent Application No. 11170650.3, dated Dec. 15, 2011.
Search Report of corresponding International Patent Application No. PCT/EP2012/051726, mailed Sep. 14, 2012.

* cited by examiner

*Primary Examiner* — Isaac Shomer
*Assistant Examiner* — Michael P Cohen
(74) *Attorney, Agent, or Firm* — Sandra B. Weiss

(57) ABSTRACT

The present invention details the use of starch silicate and starch siliconates in personal care formulations to enhance or provide aesthetic properties to skin care products. These properties can range from smoothness and silky feel to non-greasy and non-oily. These starch derivatives provide an alternative to organically modified starches which can be expensive to prepare and require the addition of inorganic salts to functionalize the reagents.

28 Claims, 1 Drawing Sheet

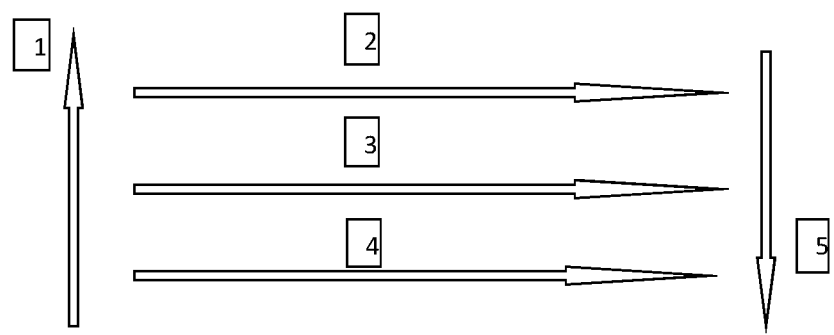

US 9,744,114 B2

MODIFIED STARCHES FOR USE IN PERSONAL CARE APPLICATIONS

This application is a National Phase Application of PCT Application No. PCT/EP2012/051726, filed Feb. 2, 2012, and claims the benefit of priority to U.S. Provisional Patent Application No. 61/439,116, filed Feb. 3, 2011 and EP Application No. 11170650.3, filed Jun. 21, 2011. Each of these applications is hereby incorporated by reference in its entirety herein.

FIELD OF INVENTION

The present invention relates to the personal care formulations comprising starches that have been modified with siliconates or silicates. In particular, the invention relates to the use of starches modified with silicones or silicates as aesthetic enhancers in skin care products.

BACKGROUND

Starches that have been modified with octenylsuccinic anhydride and then treated with aluminum sulfate are known in the literature as flow aids and for aesthetic improvements to personal care formulations. One such example has been sold under the tradename of DRY-FLO® by National Starch and Chemical Co (Bridgewater, N.J.).

A similar chemistry has been used to prepare a calcium based starch derivative using dodecenyl succinic anhydride as an alternative to the octenyl derivative, for example as disclosed in U.S. Pat. No. 5,776,476.

However, there continues to be a need for an alternative to organically modified starches which can be expensive to prepare and require the addition of inorganic salts to functionalize the reagents.

SUMMARY OF THE INVENTION

Accordingly, the present invention relates to a personal care formulation comprising a starch modified with silicate or siliconate and a cosmetically acceptable carrier, which can provide a variety of aesthetic properties to the formulation. The present invention provides personal care formulations that provide a safe and inexpensive starch derivative that will provide aesthetic benefits, such as smoothness, creaminess or being non-sticky and/or non-oily, to the personal care formulations.

DESCRIPTION OF THE FIGURE

FIG. 1 illustrates a pattern of samples discharged from the electronic pipettes in Step "11." of the Procedure for the Spreadability Test of Example 3 herein.

DETAILED DESCRIPTION OF THE INVENTION

The invention relates to a silicate or siliconate modified starch that is compatible with a wide variety of skin care ingredients and provides good aesthetic properties in a personal care formulation.

For the purposes of this invention, aesthetic properties are defined as being anything that has a positive effect on the user's perceived sensation of the formulation on the skin. Such perceptions are often described as smoothness, creaminess or as being non-sticky and/or non-oily. For example, in an embodiment, the benefit of the aesthetic enhancing starches of this invention will be noticeable when a skin care product is applied to the skin and rubbed in to form a thin film. As another example, in another embodiment, in formulations where the product is a foam or mousse, the aesthetic properties may relate to the foam volume, foam stability and spreadability, oil mitigation or silky afterfeel.

The aesthetic enhancing starches of this invention can be prepared from any starch source. Suitable starches include, but are not limited to, corn, wheat, rice, tapioca, potato, sago, pea or sweet potato. In an embodiment, the starch is corn, potato, wheat rice or tapioca. In another embodiment, the starch is tapioca.

For purposes of this invention the base starch can be native, chemically or physically modified before it is treated with the silicate or siliconate reagents. Such starch modifications may be as described in "Modified starches: Properties and Uses", O. B. Wurzburg, CRC Press, 1986, Boca Raton, Fla., (Chapters 2-9) which is incorporated by reference in its entirety herein. Suitable starch modifications include, but are not limited to, etherification, esterification and degradation by action of acids, oxidizers, and enzymes. Physical modifications may include heat treatment, grinding, hammer milling and dextrinization (heat and acid treatment) and other similar processes.

For the aesthetic enhancing starch to be functional in this invention, the starch must still have its granular structure intact. For purposes of this invention, the granular structure is defined as the form the starch has when isolated from the plant source. One way of characterizing this property is based on insolubility in water below the gelatinization temperature, and/or the presence of Maltese crosses, or birefringence when the granules are viewed under polarized light. These Maltese crosses are indicative of the highly crystalline structure of the starch.

The starch derivatives of this invention can be prepared by any number of techniques described in the literature, for example by aqueous slurry reaction conditions at either high or low pH, or under dry heat reaction conditions. In an embodiment, the base starch may be treated with at least one alkali alkyl siliconate or alkali alkyl silicate in an aqueous slurry at about 60° C. and agitated for about 8 hours. The pH of the reaction can be alkaline (e.g., pH 8-11) or near neutral by addition of a mineral acid. The modified starch is isolated from the aqueous slurry by filtration and then dried. Some examples of the preparation of the starch siliconates are U.S. Pat. No. 3,071,492 to K. P. Satterly and U.S. Pat. No. 7,375,214 to L. T. Lewis, which are each incorporated herein by reference in their entireties. Preparation of starch silicates can also be found in US Publication No. 2007/0246179 to Silenious et al., which is incorporated by reference in its entirety herein, in which the composite is prepared by precipitating silica or silicates onto the surface of the starch granule. In an embodiment, the starch is treated with sodium methyl siliconate. In another embodiment the silicate will be methyl sodium silicate or ethyl sodium silicate.

The aesthetic enhancing starch of this invention is prepared by the above methods by treating the starch with an effective amount of reagent to impart the desired properties to the personal care formulation. In an embodiment, the starch will be treated with from about 0.1 to about 5.0 percent of the methyl siliconate calculated based on the dry weight of starch. In another embodiment, the aesthetic enhancing starch is prepared by treating the base starch with from about 0.2 to about 1.0 percent of the methyl siliconate calculated based on the dry weight of the starch.

In an embodiment, the starch derivatives have a coefficient of friction of less than about 0.45, as measured by the Coefficient of Friction Testing Procedure described hereinbelow. In another embodiment, the coefficient of friction is less than about 0.37. In yet another embodiment, the coefficient of friction is less than about 0.20.

In an embodiment, the aesthetic enhancing starch is added to the personal care formulation in an effective amount that does not produce any appreciable adverse effects, such as cloudiness or flaking. In an embodiment, the modified starch will be present in the formulation from about 0.1 to about 25 percent by weight of the total formulation weight. In another embodiment the aesthetic enhancing starch will be present in the formulation from about 0.5 to about 10 percent by weight of the total formulation weight.

In an aspect of the invention, hair and skin care compositions incorporating the aesthetic enhancing starches of the present invention can be formulated with any cosmetically acceptable carrier which is inert to the aesthetic enhancing starches and to the hair or skin, as the case may be. By "cosmetically acceptable" is meant that the carrier is inert to the skin or hair and permits easy, even application to the skin or hair of a thin film which contains the reaction product. Such carriers can comprise any of a large variety of forms, including oil-in-water emulsions, water-in-oil emulsions, anhydrous or substantially anhydrous compositions such as oil-based liquids, slurries, powders or pastes, and aqueous solutions, slurries and pastes.

The aesthetic enhancing starch will find use in many personal care formulations, such as in hair care or skin care formulations. In an embodiment of the invention, the starch may be included in personal care formulations that are emulsions, such as creams and lotions and the like. In such embodiments, the starch may be present in an amount from about 0.1 to about 20 weight percent, in another embodiment from 0.5 to about 15 weight percent and in yet another embodiment from 1 to about 10 weight percent, based on total weight of the formulation.

In another embodiment, the starch may be included in personal care formulations that are oil-based substantially anhydrous formulations, such as ointments and the like. For purposes of this invention, "substantially anhydrous" means that the water content is less than about 1 weight percent, based on total weight of the formulation. In such embodiments, the starch may be present in an amount from about 5 to 75 weight percent, in a further embodiment from about 10 to about 50 weight percent and in yet another embodiment from about 10 to about 30 weight percent, based on total weight of the formulation.

In still another embodiment, the starch may be included in personal care formulations that are powders, such as aerosol or non-aerosol dry shampoos or color cosmetic skin care formulations and the like. In such embodiments, the starch may be present in an amount from about 0.1 to about 99 weight percent, in another embodiment from about 5 to 95 weight percent, and in yet another embodiment from 10 to 90 weight percent, based on total weight of the formulation.

Some examples of skin care formulations of the present invention include, but are not limited to, sun screens, moisturizing lotions, acne creams, mascara, lipsticks, foundations, or blush type powders or cakes, antibacterial ointments, defoliants, antiperspirants. The topical or cosmetic composition may contain one or more skin care additives, which are agents that provide benefits to the skin, rather than merely improving the physical or aesthetic characteristics of the topical composition. If present, such skin care actives may range from about 0.01 to 50%, preferably from about 0.05 to 35% by weight of the total composition. Exemplary skin care additives that can be used in the topical or cosmetic compositions of the present invention include, but are not limited to: self-tanning agents (e.g. dihydroxy acetone), anti-aging agents, DNA-repair enzymes, anti-wrinkle agents, anti-acne agents (e.g., resorcinol, salicylic acid, and the like), enzyme-inhibiting agents, collagen-stimulating agents, agents for the eradication of age spots and keratoses, analgesics, anesthetics, antimicrobials (e.g., antibacterials, antiyeast agents, antifungal agents, and antiviral agents), antidandruff agents, antidermatitis agents, antipruritic agents, antiemetics, anti-inflammatory agents, antihyperkeratolytic agents, antiperspirants, antipsoriatic agents, antiseborrheic agents, antihistamine agents, skin lightening agents, depigmenting agents, skin soothing/healing agents (e.g., aloe vera extract, allantoin, and the like), corticosteroids, hormones, antioxidants, proteins or peptides, vitamins and derivatives thereof (e.g., vitamin A, vitamin E, vitamin B3, vitamin B5, and the like), exfoliants, retinoids (e.g., retinoic acid and retinol), farnesol, bisabolol, phytantriol, glycerol, urea, guanidine (e.g., amino guanidine), clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, minocycline, hydroquinone, naproxen, ibuprofen, theophylline, cromolyn, albuterol, topical steroids (e.g., hydrocortisone, hydrocortisone 21-acetate, hydrocortisone 17-valerate, and hydrocortisone 17-butyrate), betamethasone valerate, betamethasone diproprionate, benzoyl peroxide, crotamiton, propranolol, promethazine, and mixtures or derivatives thereof. In an embodiment of the present invention, the topical composition comprises one or more skin care actives selected from the group consisting of self-tanning agents, anti-aging agents, DNA repair enzymes, anti-wrinkle agents, anti-acne agents, antimicrobials, anti-inflammatory agents, skin-lightening agents, antioxidants, proteins or peptides, vitamins and derivatives thereof, exfoliants, and mixtures thereof.

In another embodiment, the aesthetic enhancing starch may be included in a hair care formulation, such as a dry shampoo formulation, along with one or more cosmetically acceptable ingredients or carriers. For example, a dry shampoo may, in addition to the starch, optionally include at least one solvent, such as ethanol, at least one emulsifier, such as magnesium stearate, and optionally one or more propellants and combinations or mixtures thereof. In an embodiment, the dry shampoo formulation is either an aerosol dry powder shampoo in which the formulation includes a propellant, or the dry shampoo powder formulation is a non-aerosol dry powder shampoo which does not include a propellant.

In yet another embodiment, the aesthetic enhancing starch may be included in skin care formulations along with one or more cosmetically acceptable ingredients or carriers. For example, in addition to the starch, a color cosmetic skin care formulation may include at least one pigment, one or more fillers, one or more emulsifiers, and/or one or more emollients and combinations or mixtures thereof.

In the range of personal care formulations, e.g. in either skin care formulations and/or hair care formulations suitable for use for the present invention, the cosmetically acceptable carrier may be a pure solvent or a mixture of materials. The carrier may be in the form of an emulsion, a paste, cream, solution, or similar forms found within the personal care industry. Suitable components of the cosmetically acceptable carrier include, but are not limited to: moisturizing agents, astringent agents, chelating agents, sequestrants, emollients, preservatives, stabilizers, abrasives, adsorbents, thickeners, gellants, solidifying/structuring agents, anti-caking agents, anti-foaming agents, pH buffering/adjusting agents, binders, film formers, humectants, pigments, opacifiers, essential oils, fragrances, and aromatic compounds. In an embodiment, the cosmetically acceptable carrier may be present in the topical or cosmetic composition of the present invention at an amount ranging from about 1% to about 99.9%, in another embodiment from about 50% to about 99.5%, in yet another embodiment from about 70% to about 99%, and still yet another embodiment from about 80% to 90% by total weight of the topical or cosmetic composition.

The cosmetically acceptable carrier may also contain one or more oils, which are also known as skin conditioning agents, such as volatile or nonvolatile silicones, esters, paraffinic hydrocarbons, vegetable oils, and synthetic oils. Suitable volatile or nonvolatile silicones include, but are not limited to: cyclomethicone; methyl trimethicone; octamethyltrisiloxane; decamethyltetrasiloxane; dodecamethylpentasiloxane; dimethicone; phenyl trimethicone trimethylsiloxyphenyl dimethicone; phenyl dimethicone; cetyl dimethicone; dimethicone copolyol, cetyl dimethicone copolyol; glycerolated silicones such as lauryl PEG-9 polydimethylsiloxyethyl dimethicone; or mixtures thereof. In an embodiment, the composition may contain one or more nonvolatile silicone oils having a viscosity ranging from about 5 to 250,000 cst at 25° C. Examples include dimethicone, phenyl trimethicone, diphenyl dimethicone, and the like. Suitable esters include mono-, di-, or triesters. Monoesters are in the general form RCO—R' wherein R and R' are each independently a C1-45 straight or branched chain, saturated or unsaturated alkyl. Diesters may be formed by the reaction of a C1-45 aliphatic or aromatic mono- or dihydric alcohol with a C1-45 aliphatic or aromatic mono- or dicarboxylic acid, as appropriate, where the aliphatic group may be straight or branched chain, or saturated or unsaturated. Suitable triesters include the reaction products of a C1-45 aliphatic or aromatic alcohol having at least three hydroxyl groups with a C1-45 carboxylic acid, or a C1-45 aliphatic or aromatic alcohol with a C1-45 tricarboxylic acid, with the aliphatic chains being linear or branched, saturated or unsaturated. Examples include esters of caprylic and capric acids and glycerin such as caprylic/capric triglycerides; esters of glycerin or polyglycerin and stearic acid such as glyceryl stearate, diglyceryl diisostearate; esters of malic acid and isostaryl alcohol such as diisostearyl malate; coco caprylate caprate and the like. If present, such oils may range from about 0.1 to 99% by total weight of the composition. The cosmetically acceptable carrier may also comprise one or more humectants, which include, but are not limited to: glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as C1-6 alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and the like. In an embodiment, the humectants used in the composition of the invention are C1-6, preferably C2-4 alkylene glycols, most particularly butylene glycol, or glycerin. If present, such humectants may range from about 0.001% to about 25%, in another embodiment from about 0.005% to about 20%, and in yet another embodiment from about 0.1% to about 15%, by total weight of the topical composition.

The cosmetically acceptable carrier may also comprise one or more organosiloxane elastomers, generally those known as non-emulsifying. If present, such elastomers may range from about 0.1 to 30% by weight of the total composition. Examples of suitable elastomers include, but are not limited to dimethicone/vinyl dimethicone crosspolymer, methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, and the like.

The compositions of the invention may also contain other optional ingredients such as structuring agents in the form of polymeric structuring agents, such as acrylic polymers, polyamides or polyurethanes. The structuring agents may be water or oil soluble or dispersible. Such structuring agents will provide structure, or increase the viscosity of the composition. The structuring agents may be present from about 0.1 to 50%, in another embodiment from about 0.5 to 40%, and in yet another embodiment from about 1 to 35% by weight of the total composition. Suitable structuring agents include natural, synthetic waxes, or mineral waxes such as petrolatum, candelilla, ozokerite, synthetic wax, polyethylene, silicone waxes such as stearyl or behenyl dimethicone, and the like. Suitable polymeric structuring agents include carbomer, acrylic polymers or copolymers, such as acrylates copolymer, polyacryalte-1 crosspolymer, acrylates/C10-30 alkyl acrylate crosspolymer, C10-30 alkyl acrylate crosspolymer (e.g., those commercially available as Carbopol® or Pemulen®), ester or amide terminated polyamides (those commercially available from Arizona Chemical under the Uniclear® or Sylvaclear®), or aqueous dispersions or solutions of polyurethanes.

The present invention will now be illustrated by the following examples. The examples are intended to exemplify the present invention but are not intended to limit the scope of the invention in any way. The breadth and scope of the invention are to be limited solely by the claims appended hereto.

EXAMPLES

Example 1

Preparation of Starch Siliconate

A total of 500 grams of tapioca starch is added to a 2 L plastic beaker and 750 mLs of DI water at 23° C. is added with agitation from an overhead stirrer. Once the slurry is uniform 20 grams of sodium methyl siliconate is added slowly by sprinkling the powered over the surface. The total addition time of the 20 grams will take approximately 5 minutes and must be done slowly to avoid localized high concentrations. The beaker is heated to 45° C. in a water bath while maintaining the agitation and allowed to react overnight (12 hours). The slurry is then pH adjusted with dilute HCl (0.1 N) to obtain a pH of between 6.0 and 7.0. The slurry is filtered through a paper filter and the resulting cake is washed with 2 L of DI water. The wet cake is crumbled onto a piece of kraft paper and allowed to dry overnight or until the moisture content of the starch is below 15% (as measured by oven solids).

Example 2

Preparation of a Starch Silicate

A total of 500 grams of tapioca starch is slurried into 750 mL of DI water in a plastic beaker and mixed with an overhead stirrer. Once the slurry is uniform, 20 grams of methyl sodium silicate is added to the slurry and the pH is adjusted to about 7.0 with dilute HCl (0.1N). The starch is then filtered through a paper filter and then crumbled onto aluminum foil. The starch is placed in a force air oven preheated to 80° C. for two hours. The oven is then heated to 105° C. and the starch is allow to heat for an additional 4 hours. After the allotted time, the starch is removed from the oven and allowed to cool to room temperature.

Example 3

Spreadability Test

The spreadability test measures the resistance of a skin care formula and simulates the spreading of such a product on the skin such as the application of a hand cream. The test was accomplished with the procedure below using a Stable Micro System's Texture Analyzer model TA.XT.PLUS and software package—Exponent Micro Systems Version 4.0.3.0 (distributed by Texture Technologies Corp of Scarsdale, N.Y.).

Procedure for the Spreadability Test
1. Select the "Friction Rig Test" test from the tests options listed.
   a. The Friction Rig Test is a special test that allows the T.A to collect data on how spreadable a sample is by dragging a device across the sample and collecting data on how hard it was to drag it.
   b. A Return to Start test will start the T.A arm a certain distance from the sample and penetrate it a specific distance. It will then return to its origin.
   c. Click on the "Advanced Options" pull down and make sure it is "On".
   d. Change the settings to the following values:
      i. Test Mode: Tension
      ii. Test Speed: 5
      iii. Post Test Speed: 5
      iv. Target Mode: Distance
      v. Distance: 95
      vi. Trigger Type: Button
      vii. Break Mode: Off
      viii. Stop Plot At: Start Position
      ix. Tare Mode: Auto
      x. Advanced Options: On
2. Once all the correct values have been filled in, click the "Update Project" button in the lower left corner.
3. Now in the left hand menu, click on the "Test Configuration" stoplight icon.
   a. The Test Configuration window allows the operator to specify the file names the program will save the data to. It also provides some extra parameters and it is where the data acquisition rate can be specified (this is how fast the T.A collects data).
   b. The "File ID" names should be of the format below:
      i. Type of Test_Test_Number_date_product_notebook # For example: Spread_1_071607_ProductA_3564871
      ii. The Exponent software will automatically add a test number to the end of each of the save files for each separate test. For example: File ID=Spread_1_071607_ProductA_3564871. However, once the test is run, Exponent will save the file as: Spread_1_071607 ProductA_35648711. Notice the extra "1" at the end.
   c. "File #" should equal 1 and "Format" should be left blank.
   d. Make sure that the "Auto Save" checkbox is checked. If it is not, check it.
   e. Where it says "Path", click on the arrow to the right of it and manually select the save location of the data. The save location should be the new folder created at the beginning of the SOP.
   f. The "Title" text should match the "File ID" name so type in the same text.
   g. For the "Batch" option, the "Use File ID" checkbox to the right should be checked. If not, check it.
   h. Go back the "archive information" tab. Click "Apply", click "OK" then click "OK" again.

Instructions on Setting Up the Spreadability Rig
4. Screw in the connector probe to the hole on the T.A arm closest its body.
5. The T-Fixture should be connected to the T.A as shown below. Notice the screws are lined up to the far right side so that the screw actually hits the right side of their fixture. If they are not lined up to the right, the leg height will need to be adjusted. This can be done by simply turning the leg left or right until an even horizontal plane is obtained once the machine is turned on its side.
6. Carefully, turn the machine on its side so that the extra leg on the T-Fixture is supporting the weight. This is apparent in the images on the following page.
7. Using the long screw and flat-head screw driver attach the sled fixture to the connector probe.
8. Place the long glass plate under the sled fixture and clamp it at the far end on both sides.

Calibrate the Distance
9. It is now necessary to calibrate the distance.
   a. Place the sled fixture on the glass and use the arrows on the T.A to move it so the end is an inch from the wall.
   b. To calibrate the distance, go to the top pull down menu and select:
      "T.A"→"Calibrate"→"Calibrate Height"
      i. Enter the following values:
         "Return Distance (mm)"=10
         "Return Speed (mm/sec)"=10
         "Contact Force (g)"=1
         Click "OK"
   c. The arm will move to the right until it contacts the platform, and then move back to the left. The wall on the platform is now referenced as the zero point.
10. To pre-set the starting distance go to the top pull down menu: "T.A"→"Move Probe"
   a. This function allows the operator to move the T.A arm using the slider. However, this function will mainly be used to pre-set a start distance so that all of the tests begin at the same distance.
   b. To do this click on: "Mem"→"Set Up" and the "Pos 1" tab should be selected.
      i. Enter the Following:
         "Distance"=10 (mm)
         "Force"='LEAVE BLANK' (←really leave it blank!)
         "Speed"=40 (mm/sec)
   c. Click on the "Pos 2" tab ii. Enter the Following:
   "Distance"=100 (mm)
   "Force"='LEAVE BLANK'
   "Speed"=40 (mm/sec)
   Click "OK"
d. While still in the "Move Probe" window, go to "Mem-"→"Location 1:"→Click on "Move to position 10 mm at 40 mm/sec". (Confirm the T.A arm has moved to a position right before the wall.

Running the Test

Place a piece of tape on the side of the glass where the back (part closest to hinge) of the sled fixture sits.
11. Lift the sled fixture and follow the directions below:
   a. Using a 2.5 mL tip for the electronic pipette set the pick up amount to 2.5 mL and the discharge amount to 0.25 mL.
   b. Pipette a pattern similar to the one illustrated in FIG. 1. Each number represents the end of a 0.25mL line.
12. Carefully lay the sled fixture down on top of the sample and press on it gently for 2 seconds.
13. Go to the top pull down menu: "T.A"→"Run a Test"
   a. Check to make sure all the file names are correct and auto-save is checked.
   b. Click "Run a Test".
14. The first run should only spread out the sample a little bit. Once the probe has returned to its starting position and the test has officially stopped, add a 200 g weight to the center or the rectangular sled fixture. This helps to compress the sample so that a real friction reading can take place.
15. Click "Control+Q" on the keyboard. This will perform a quick test. This is done so that nothing is changed but the run number which Exponent updates automatically.
16. Repeat the previous step 3 more times for a total of 5 runs.
17. Once 5 runs (total) have been performed, lift the sled fixture and clean off the glass and it using paper towels, Kimwipes and acetone if necessary. 5 runs are considered one whole test. If the next test is with a different lotion, then either acetone, or soap and water can be used after removing the glass from the machine.
18. Repeat the test two more times for a total of three full tests (15 runs total).
19. For every new sample, start at "Section 5C: 3" and proceed accordingly.
20. When the tests for the day are fully done, clean all equipment and remove the spreadability rig from the T.A.

Results:
Comparison of Tapioca OSA Versus Tapioca Siliconate Formulation:
1. In main beaker, all Phase A ingredients were added except xanthan gum. Mix on homogenizer to a uniform paste at low to moderate speed and heating to 75-80° C. Sprinkle in xanthan gum and continue mixing at low to moderate speed until fully hydrated.
2. In a side beaker, add the Phase B ingredients and mix the liquid with a propeller blade at low speed then heat to 75-80° C.
3. Once Phase A and Phase B reach desired temperature, add Phase B to Phase A with moderate homogenization. Mix for 10 minutes and then cool to 65° C.
4. When the batch reached 65° C., sprinkle in Phase C and homogenize at low to moderate speed for 10 minutes until hydrated.
5. Pre-mix Phase D in a separate beaker and then add to the main batch once step 4 above is complete.
6. When the batch is homogeneous, cool to 45° C. and add Phase E. Homogenize moderately until fully dispersed.
7. Switch batch to sweep mixing U-blade and continue mixing at low speed while cooling to 25° C.

TABLE 1

| Ingredient # | Raw Material Name | Wet % | Wet Wt | Units |
|---|---|---|---|---|
| | Phase A | | | |
| 1 | DI Water (Aqua) | 65.40% | 98.10 | g |
| 2 | Glycerine | 5.00% | 7.50 | g |
| 3 | Phenoxyethanol (and) Methylparaben (and) Ethylparaben (and) Butylparaben (and) Propylparaben (and) Isobutylparaben | 1.00% | 1.50 | g |
| 4 | Xanthan Gum | 0.10% | 0.15 | g |
| | Phase B | | | |
| 5 | Glyceryl Stearate (and) PEG-100 Stearate | 2.00% | 3.00 | g |
| 6 | *Persea Gratissima* (Avocado) Oil | 6.00% | 9.00 | g |
| 7 | *Simmondsia Chinensis* (Jojoba) Seed Oil | 6.00% | 9.00 | g |
| 8 | *Olea Europaea* (Olive) Fruit Oil | 7.00% | 10.50 | g |
| 9 | Dimethicone | 1.00% | 1.50 | g |
| | Phase C | | | |
| 10 | Carbomer | 0.20% | 0.30 | g |
| | Phase D | | | |
| 11 | Water (Aqua) | 1.00% | 1.50 | g |
| 12 | Triethanolamine | 0.30% | 0.45 | g |
| | Phase E | | | |
| 13a | Tapioca treated w/2% OSA and 1% aluminum sulfate | 5.00% | 7.50 | g |
| 13b | Tapioca treated w/1% methyl siliconate | 5.00% | 7.50 | g |
| | TOTALS: | 100.00% | 150.00 | g |

TABLE 2

| Product | Spreadability Result (average) |
|---|---|
| Tapioca (2% OSA, 1% Aluminum sulfate) 13a | 26.28 |
| Tapioca (1% Methylsiliconate) 13b | 24.78 |

The results from the above spreadability test, as shown in Table 2, demonstrate that the sample containing the aesthetic OSA tapioca (13a) starch does not perform as well as the siliconate modified tapioca. This finding represents the aesthetic properties of smoothness, creaminess and lubricity that is provided by the tapioca siliconate in skin care formulations.

Example 4

Coefficient of Friction

Coefficient of Friction Testing Procedure is a proprietary procedure run by the Falex Corporation of Sugar Grove, Ill. as a for-fee service using a Falex Multi-specimen Test Machine, Lever Load Version.

TABLE 3

| Product | Coefficient of Friction value |
|---|---|
| Corn Starch | 0.630 |
| Tapioca Starch | 0.349 |
| Corn Starch treated with 1% methyl siliconate | 0.352 |
| Tapioca Starch treated w/1% methyl siliconate | 0.183 |

The results from Table 3 above show that the treatment of native starch with methyl siliconate provides a significant reduction in the coefficient of friction compared to the same type of native starch that has not been treated, which relates to smoother, silkier feel on the skin.

Example 5

Dry Shampoo Formulation

An example of a dry shampoo formulation according to the invention was prepared including the components shown in Table 4.

TABLE 4

| Trade Name | Raw Material Name | Wet % | Wet Wt. |
|---|---|---|---|
| Concentrate phase | | 40.00% | 400.00 |
| DRY-FLO ® TS starch | Tapioca Starch Polymethylsilsesquioxane | 4.50% | 45.00 |
| TAPIOCA PURE starch | Tapioca Starch | 1.00% | 10.00 |
| Ethanol Anhydrous 40-B | SD Alcohol 40-B (Alcohol Denatured) | 32.00% | 320.00 |
| Magnesium Stearate NF (FCC Kosher) | Magnesium Stearate | 2.50% | 25.00 |
| Propellant | | 60.00% | 600.00 |
| A-46 | Isobutane (and) Propane | 60.00% | 600.00 |
| TOTALS: | TOTALS: | 100.00% | 1000.00 |

The formulation was made according to the following procedure:
1. Vessel was charged with ethanol
2. Begin mixing with a homogenizer.
3. While mixing ethanol, slowly sift in all materials in the concentrate phase until all components have been fully dispersed.
4. Once all ingredients have been added, continue to mix for about 10 minutes.
5. Fill cans with mixture and charge with propellant A-46.

Example 6

Body Powder Formulation

An example of a body powder formulation according to the invention was prepared including the components shown in Table 5.

TABLE 5

| Trade Name | Raw Material Name | Weight % | Actual weight (g) |
|---|---|---|---|
| DRY-FLO ® TS starch | Tapioca Starch Polymethylsilsesquioxane | 88.00% | 880.40 |
| Kaolin, Colloidal USP BC 2749 | Kaolin | 5.00% | 50.10 |
| Sericite SL | Mica | 2.00% | 20.07 |
| Titanium Dioxide 325 USP | Titanium Dioxide | 2.00% | 20.03 |
| Colorona ® Carmine Red | Pigment | 1.00% | 10.20 |
| TAPIOCA PURE starch | Tapioca Starch | 2.00% | 20.08 |
| TOTALS: | | 100.00% | 1000.88 |

The formulation was made according to the following procedure:
1. All ingredients were combined in the vessel.
2. The ingredients were blended together until uniform.

Example 7

Sunscreen Formulation

An example of a body powder formulation according to the invention was prepared including the components shown in Table 5.

| Trade Name | Raw Material Name | Weight % | weight (g) |
|---|---|---|---|
| Phase A | Phase A | 58.45% | 1052.10 |
| Deionized Water | Water (Aqua) | 50.65% | 911.70 |
| Propylene Glycol | Propylene Glycol | 2.00% | 36.00 |
| Phenonip | Phenoxyethanol (and) Methylparaben (and) Ethylparaben (and) Butylparaben (and) Propylparaben (and) Isobutylparaben | 1.00% | 18.00 |
| Dissolvine ® NA2-S | Disodium EDTA | 0.10% | 1.80 |
| Carbopol 940 | Carbomer | 0.30% | 5.40 |
| DERMACRYL ® AQF (45% active) polymer | Acrylates Copolymer | 4.40% | 79.20 |
| Phase B | Phase B | 34.10% | 613.80 |
| Neo Heliopan ® 303 | Octocrylene | 2.00% | 36.00 |
| Neo Heliopan ® HMS | Homosalate | 12.00% | 216.00 |
| Neo Heliopan ® 357 | Avobenzone | 3.00% | 54.00 |
| Neo Heliopan ® BB | Benzophenone-3 | 4.00% | 72.00 |
| Neo Heliopan ® OS | Ethylhexyl Salicylate | 5.00% | 90.00 |
| Finsolv TN | C12-15 Alkyl Benzoate | 5.00% | 90.00 |
| Arlacel 165 | Glyceryl Stearate (and) PEG-100 Stearate | 3.10% | 55.80 |
| Phase C | Phase C | 2.45% | 44.10 |
| Deionized Water | Water (Aqua) | 2.00% | 36.00 |
| Triethanolamine-99% | Triethanolamine | 0.45% | 8.10 |
| Phase D | Phase D | 5.00% | 90.00 |
| DRY-FLO ® TS starch | Tapioca Starch Polymethylsilsesquioxane | 5.00% | 90.00 |
| TOTALS: | TOTALS: | 100.00% | 1800.00 |

The formulation was made according to the following procedure:
1. Add Deionized Water with Propylene Glycol, Disodium EDTA, and Phenonip to main beaker and begin heating to 75-80° C. with low homogenizer mixing (2000-3000 rpm).
2. Once dispersed, sprinkle in Carbopol 940 and homogenize at low to moderate speed (2000-3000 rpm) until hydrated.
3. Then add Dermacryl AQF to main beaker and mix until dispersed.

4. Add Phase B ingredients to side beaker and begin heating to 75-80° C. with propeller mixing at 300 rpm.
5. Once Phases A and B reach desired temperatures, add Phase B to Phase A with moderate homogenization (4000 rpm) mixing for 10 minutes at 75-80 C. Begin cooling batch to 45 C.
6. Pre-mix Phase C and add to main beaker once temperature gets below 45° C. Homogenize (4000 rpm) for 5 minutes until dispersed and uniform.
7. Add Phase D to main beaker and homogenize (4000 rpm) until fully dispersed and uniform. Switch batch to sweep blade and mix at 20 rpm while cooling to 25° C.

Although the invention is illustrated and described herein with reference to specific embodiments, the invention is not intended to be limited to the details shown. Rather, various modifications may be made in the details within the scope and range of equivalents of the claims and without departing from the spirit of the invention.

We claim:

1. A personal care formulation comprising:
   a starch modified with a siliconate, and further comprising
   a cosmetically acceptable carrier wherein the cosmetically acceptable carrier is an oil-in-water emulsion, a water-in-oil emulsion, an anhydrous powder composition or a substantially anhydrous powder composition having a water content less than 1% based on total weight of the composition,
   wherein said personal care formulation is selected from the group consisting of a skin care formulation and a hair care formulation,
   wherein the starch is tapioca.

2. The personal care formulation of claim 1 wherein the starch is modified with at least one alkali metal alkyl siliconate.

3. The personal care formulation of claim 1 wherein the starch is modified with from 0.1 to 5.0 weight percent of a methyl siliconate, based on the weight of the starch.

4. The personal care formulation of claim 3 wherein the starch is modified with from 0.2 to 1.0 weight percent of the methyl siliconate, based on the weight of the starch.

5. The personal care formulation of claim 1 wherein the modified starch is present in an amount from 0.1 to 25 percent by weight of the total formulation weight.

6. The personal care formulation of claim 1 wherein the formulation is a color cosmetic powder further comprising at least one pigment.

7. The personal care formulation of claim 1 wherein the formulation is a cream or a lotion in form of an emulsion.

8. The personal care formulation of claim 1 wherein the formulation is a dry shampoo powder formulation.

9. The personal care formulation of claim 8 where the formulation further comprises a propellant.

10. The personal care formulation of claim 1 wherein the modified starch has a coefficient of friction of less than 0.45.

11. A personal care formulation comprising:
    a starch modified with a siliconate, and further comprising
    a cosmetically acceptable carrier wherein the cosmetically acceptable carrier is an oil-in-water emulsion, a water-in-oil emulsion, an anhydrous powder composition or a substantially anhydrous powder composition having a water content less than 1% based on total weight of the composition,
    wherein said personal care formulation is selected from the group consisting of a skin care formulation and a hair care formulation, and
    wherein the starch is modified with from 0.2 to 1.0 weight percent of methyl siliconate, based on the weight of the starch.

12. The personal care formulation of claim 11 wherein the starch is selected from the group consisting of corn, potato, rice, wheat and tapioca.

13. The personal care formulation of claim 11 wherein the modified starch is present in an amount from 0.1 to 25 percent by weight of the total formulation weight.

14. The personal care formulation of claim 11 wherein the formulation is a color cosmetic powder further comprising at least one pigment.

15. The personal care formulation of claim 11 wherein the formulation is a cream or a lotion in form of an emulsion.

16. The personal care formulation of claim 11 wherein the formulation is a dry shampoo powder formulation.

17. The personal care formulation of claim 16 where the formulation further comprises a propellant.

18. The personal care formulation of claim 11 wherein the modified starch has a coefficient of friction of less than 0.45.

19. A personal care formulation comprising:
    a starch modified with a siliconate, and further comprising
    a cosmetically acceptable carrier wherein the cosmetically acceptable carrier is an oil-in-water emulsion, a water-in-oil emulsion, an anhydrous powder composition or a substantially anhydrous powder composition having a water content less than 1% based on total weight of the composition,
    wherein said personal care formulation is selected from the group consisting of a skin care formulation and a hair care formulation, and
    wherein the modified starch has a coefficient of friction of less than 0.45.

20. The personal care formulation of claim 19 wherein the starch is selected from the group consisting of corn, potato, rice, wheat and tapioca.

21. The personal care formulation of claim 19 wherein the starch is modified with at least one alkali metal alkyl siliconate.

22. The personal care formulation of claim 19 wherein the starch is modified with from 0.1 to 5.0 weight percent of a methyl siliconate, based on the weight of the starch.

23. The personal care formulation of claim 19 wherein the starch is modified with from 0.2 to 1.0 weight percent of a methyl siliconate, based on the weight of the starch.

24. The personal care formulation of claim 19 wherein the modified starch is present in an amount from 0.1 to 25 percent by weight of the total formulation weight.

25. The personal care formulation of claim 19 wherein the formulation is a color cosmetic powder further comprising at least one pigment.

26. The personal care formulation of claim 19 wherein the formulation is a cream or a lotion in form of an emulsion.

27. The personal care formulation of 19 wherein the formulation is a dry shampoo powder formulation.

28. The personal care formulation of claim 27 where the formulation further comprises a propellant.

* * * * *